US009554775B2

(12) United States Patent
Nakamura et al.

(10) Patent No.: US 9,554,775 B2
(45) Date of Patent: Jan. 31, 2017

(54) ULTRASONIC TRANSDUCER ELEMENT CHIP, PROBE, ELECTRONIC INSTRUMENT, AND ULTRASONIC DIAGNOSTIC DEVICE

(71) Applicant: SEIKO EPSON CORPORATION, Tokyo (JP)

(72) Inventors: Tomoaki Nakamura, Nagano (JP); Jiro Tsuruno, Nagano (JP); Kanechika Kiyose, Nagano (JP)

(73) Assignee: Seiko Epson Corporation, Tokyo (JP)

( * ) Notice: Subject to any disclaimer, the term of this patent is extended or adjusted under 35 U.S.C. 154(b) by 0 days.

(21) Appl. No.: 14/733,014

(22) Filed: Jun. 8, 2015

(65) Prior Publication Data

US 2015/0265246 A1 Sep. 24, 2015

Related U.S. Application Data

(63) Continuation of application No. 13/804,872, filed on Mar. 14, 2013, now Pat. No. 9,079,220.

(30) Foreign Application Priority Data

Mar. 30, 2012 (JP) ................. 2012-078672

(51) Int. Cl.
*A61B 8/00* (2006.01)
*A61B 8/08* (2006.01)
*B06B 1/06* (2006.01)
*G03B 42/06* (2006.01)

(52) U.S. Cl.
CPC ........... *A61B 8/4494* (2013.01); *A61B 8/4427* (2013.01); *A61B 8/4444* (2013.01); *A61B 8/461* (2013.01); *A61B 8/5207* (2013.01); *B06B 1/0622* (2013.01); *G03B 42/06* (2013.01)

(58) Field of Classification Search
CPC ..... B06B 1/0622; A61B 8/4427; A61B 8/461; A61B 8/4444; A61B 8/4494; A61B 8/5207; G03B 42/06
See application file for complete search history.

(56) References Cited

U.S. PATENT DOCUMENTS

| 8,169,855 | B2 | 5/2012 | Nakamura |
| 9,079,220 | B2 * | 7/2015 | Nakamura ............ B06B 1/0622 |
| 2002/0014816 | A1 | 2/2002 | Takeuchi et al. |
| 2003/0033700 | A1 | 2/2003 | Takeuchi et al. |

(Continued)

FOREIGN PATENT DOCUMENTS

| EP | 1793431 A1 | 11/2006 |
| JP | 63-135609 U | 9/1988 |

(Continued)

OTHER PUBLICATIONS

The Extended European Search Report for the corresponding European Application No. 13768858.6 dated Oct. 21, 2015.

*Primary Examiner* — Daniel Pihulic
(74) *Attorney, Agent, or Firm* — Global IP Counselors, LLP

(57) ABSTRACT

An ultrasonic transducer element chip includes a substrate defining an opening, an ultrasonic transducer element disposed at a position corresponding to the opening in a thickness direction of the substrate, and a reinforcing member connected to the substrate to cover the opening. The reinforcing member defines a ventilation passage from the opening to an outside of the substrate.

10 Claims, 12 Drawing Sheets

(56) References Cited

U.S. PATENT DOCUMENTS

| | | | |
|---|---|---|---|
| 2006/0043843 A1 | 3/2006 | Sugiura et al. | |
| 2007/0040477 A1 | 2/2007 | Sugiura et al. | |
| 2007/0251324 A1 | 11/2007 | Wado et al. | |
| 2007/0299345 A1 | 12/2007 | Adachi et al. | |
| 2008/0013761 A1 | 1/2008 | Matsuzawa et al. | |
| 2008/0116765 A1 | 5/2008 | Sugiura et al. | |
| 2010/0327695 A1 | 12/2010 | Goel et al. | |
| 2011/0074246 A1 | 3/2011 | Nishie et al. | |
| 2011/0115337 A1 | 5/2011 | Nakamura et al. | |
| 2011/0125021 A1* | 5/2011 | Sudol | A61B 8/00 600/443 |
| 2013/0223191 A1 | 8/2013 | Nakamura et al. | |
| 2013/0258802 A1 | 10/2013 | Nakamura et al. | |
| 2013/0258803 A1* | 10/2013 | Nakamura | B06B 1/0622 367/7 |
| 2013/0261465 A1 | 10/2013 | Nakamura et al. | |
| 2014/0103781 A1 | 4/2014 | Nakamura et al. | |
| 2015/0265246 A1* | 9/2015 | Nakamura | B06B 1/0622 600/459 |

FOREIGN PATENT DOCUMENTS

| | | | |
|---|---|---|---|
| JP | 2002-009359 A | 1/2002 | |
| JP | 2005-354582 A | 12/2005 | |
| JP | 2006-094459 A | 4/2006 | |
| JP | 2006-332799 A | 12/2006 | |
| JP | 2009-231484 A | 10/2009 | |
| JP | 2010-183437 A | 8/2010 | |
| JP | 2010-210283 A | 9/2010 | |
| JP | 2011-077918 A | 4/2011 | |
| JP | 2011-082624 A | 4/2011 | |
| JP | 2011-124973 A | 6/2011 | |
| JP | 2011-139295 A | 7/2011 | |
| JP | WO 2013145764 A1 * | 10/2013 | ........... B06B 1/0622 |
| JP | 20140148452 A * | 12/2014 | ........... B06B 1/0622 |
| JP | 2832297 A4 * | 11/2015 | ........... B06B 1/0622 |
| WO | 2012/014111 A2 | 2/2012 | |
| WO | 2013/145763 A1 | 10/2013 | |
| WO | 2013/145764 A1 | 10/2013 | |

* cited by examiner

ULTRASONIC TRANSDUCER ELEMENT CHIP, PROBE, ELECTRONIC INSTRUMENT, AND ULTRASONIC DIAGNOSTIC DEVICE

CROSS-REFERENCE TO RELATED APPLICATIONS

This application is a continuation application of U.S. patent application Ser. No. 13/804,872 filed on Mar. 14, 2013. This application claims priority to Japanese Patent Application No. 2012-078672 filed on Mar. 30, 2012. The entire disclosures of U.S. patent application Ser. No. 13/804,872 and Japanese Patent Application No. 2012-078672 are hereby incorporated herein by reference.

BACKGROUND

Technical Field

The present invention relates to an ultrasonic transducer element chip, a probe that uses the ultrasonic transducer element chip, and an electronic instrument and an ultrasonic diagnostic device and the like that use the probe.

Related Art

As described in Japanese Laid-Open Patent Publication No. 2011-82624, for example, an ultrasonic transducer element chip is provided with a substrate. A plurality of openings are formed in the substrate. An ultrasonic transducer element is provided in each of the openings. The ultrasonic transducer element is provided with a vibrating film. The vibrating film covers the openings from a surface of the substrate.

SUMMARY

When the openings are formed in the substrate, the strength of the substrate is deteriorated. The strength is insufficient with respect to force in a thickness direction of the substrate. Therefore, when the ultrasonic transducer element chip is pressed against a target to be tested, the ultrasonic transducer element chip was sometimes damaged.

According to at least one embodiment of the present invention, an ultrasonic transducer element chip that is thin and has sufficient strength in resistance to pressing force in a thickness direction of a substrate can be provided.

According to one aspect of the present invention, an ultrasonic transducer element chip includes a substrate defining an opening, an ultrasonic transducer element disposed at a position corresponding to the opening in a thickness direction of the substrate, and a reinforcing member connected to the substrate to cover the opening. The reinforcing member defines a ventilation passage from the opening to an outside of the substrate. Through the ventilation passage, an internal space of the opening and an external space of the substrate are in communication with each other.

BRIEF DESCRIPTION OF THE DRAWINGS

Referring now to the attached drawings which form a part of this original disclosure.

DETAILED DESCRIPTION OF EXEMPLARY EMBODIMENTS

Next, embodiments of the present invention will be explained with reference to the attached drawings. The embodiments explained below shall not be construed as unreasonably limiting the subject matter of the present invention described in the claims, and all the elements explained in the embodiments are not necessarily essential to the solving means of the present invention.

(1) Overall Configuration of Ultrasonic Diagnostic Device

Figure 1:
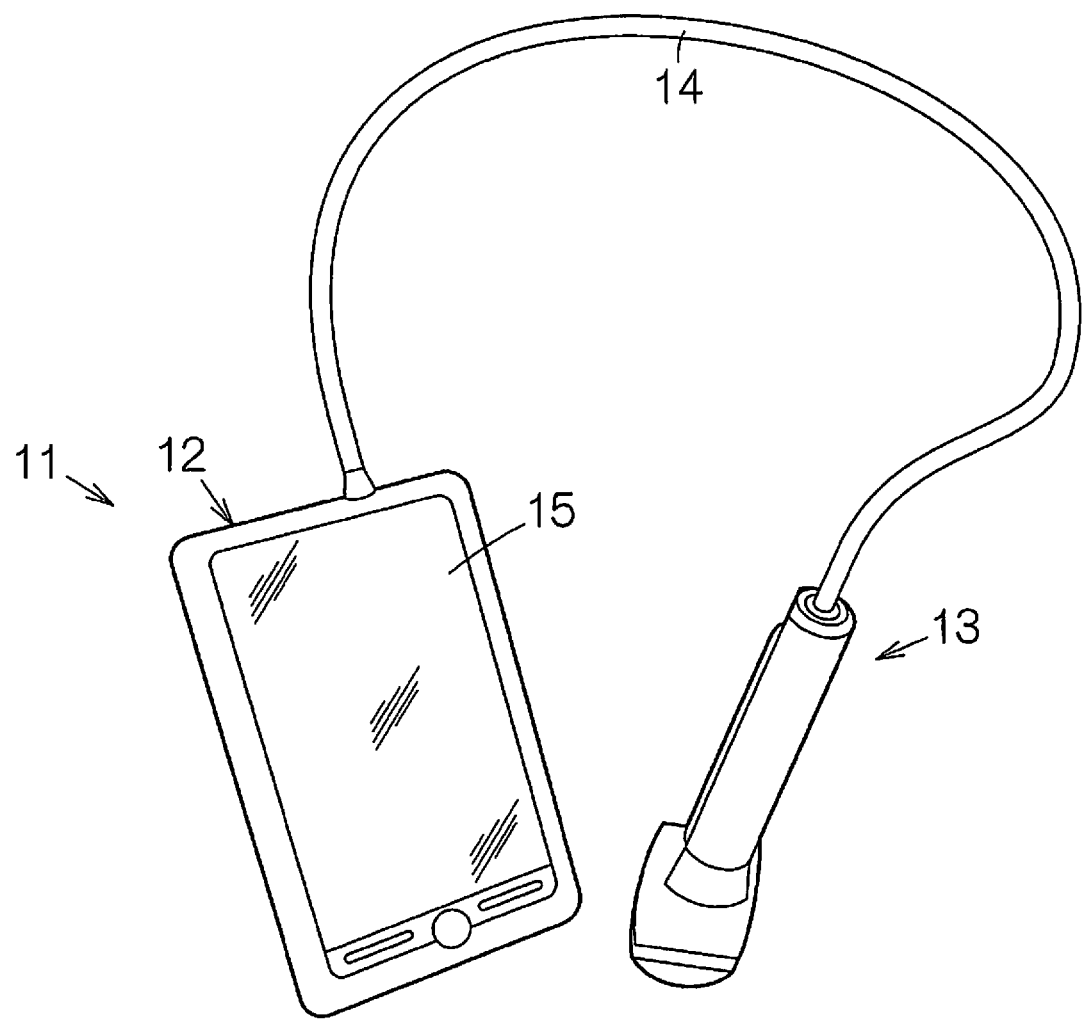
FIG. 1 is a perspective view schematically showing an example of an electronic instrument, that is, an ultrasonic diagnostic device according to one embodiment of the present invention.

FIG. 1 schematically shows a configuration of an ultrasonic diagnostic device 11 as an example of an electronic instrument according to an embodiment of the present invention. The ultrasonic diagnostic device 11 is provided with a device terminal 12 and an ultrasonic probe (probe) 13. The device terminal 12 and the ultrasonic probe 13 are connected to each other through a cable 14. The device terminal 12 and the ultrasonic probe 13 communicate an electric signal through the cable 14. A display panel (display device) 15 is incorporated in the device terminal 12. A screen of the display panel 15 is exposed on a surface of the device terminal 12. As described later, in the device terminal 12, an image is generated based on ultrasonic waves detected with the ultrasonic probe 13. Imaged detection results are displayed on the screen of the display panel 15.

Figure 2:
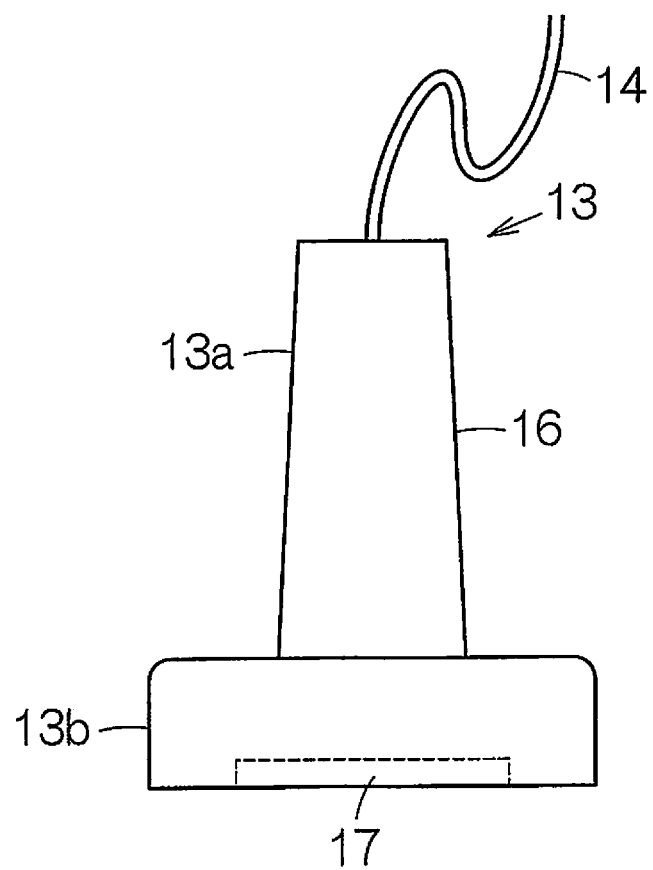
FIG. 2 is an enlarged front view of an ultrasonic probe.

As shown in FIG. 2, the ultrasonic probe 13 has a case 16 (one example of a case member). An ultrasonic transducer element chip (hereinafter referred to as "element chip") 17 is accommodated in the case 16. A surface of the element chip 17 may be exposed on a surface of the case 16. The element chip 17 outputs ultrasonic waves from the surface thereof, and receives reflected waves of ultrasonic waves.

Also, the ultrasonic probe 13 may be provided with a probe head 13b removably coupled with a probe main body 13a. In such an instance, the element chip 17 may be incorporated in the case member of the probe head 13b, which is configured to be coupled to the probe main body 13a.

(2) Configuration of Ultrasonic Transducer Element Chip of First Embodiment

Figure 3:
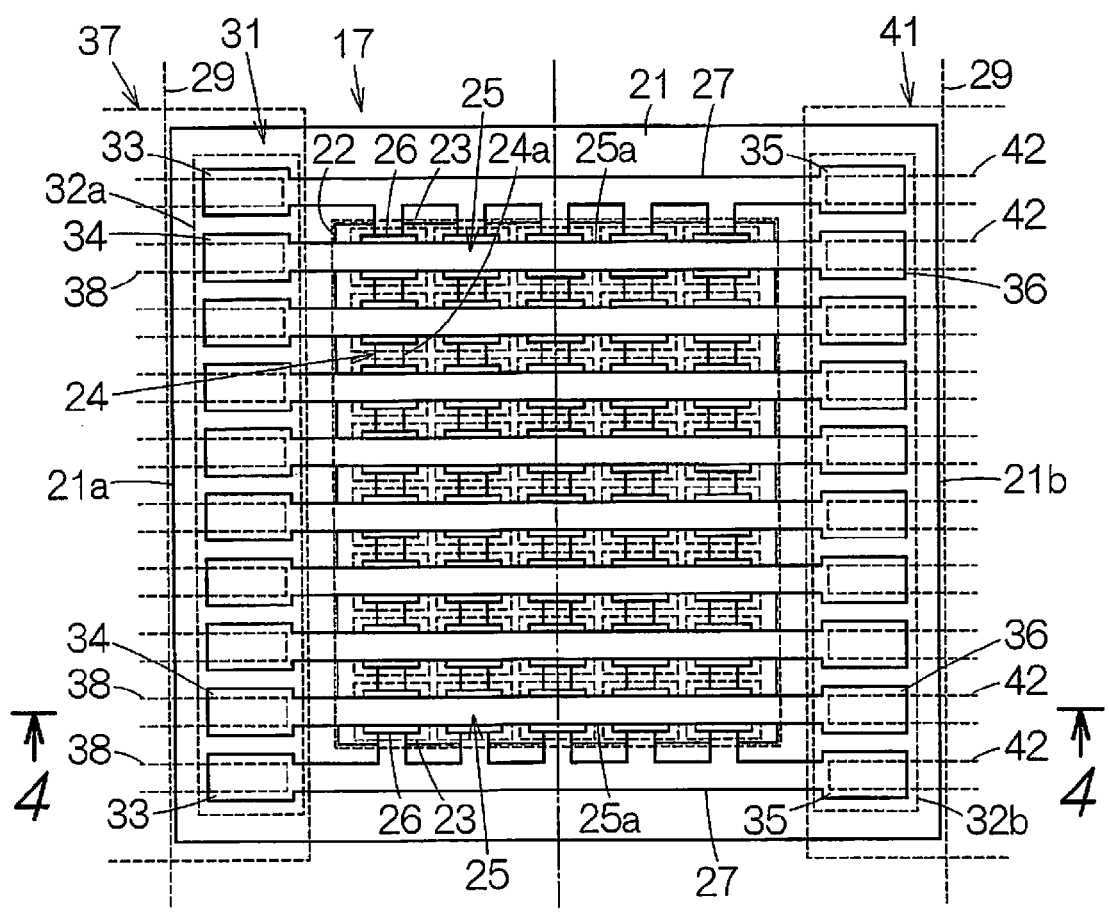
FIG. 3 is an enlarged plan view of an ultrasonic transducer element chip.

FIG. 3 schematically shows a plan view of the element chip 17 of the first embodiment. The element chip 17 is provided with a substrate 21. An element array 22 is formed on a surface (first surface) of the substrate 21. The element array 22 is constructed with an arrangement of ultrasonic transducer elements (hereinafter referred to as "elements") 23. The arrangement is formed in a matrix having a plurality of rows and a plurality of columns. Each element 23 has a piezoelectric element section. The piezoelectric element section is constructed of a lower electrode 24, an upper electrode 25, and a piezoelectric film 26. The piezoelectric film 26 is sandwiched between the lower electrode 24 and the upper electrode 25 in each element 23.

The lower electrode 24 has a plurality of first conductive bodies 24a. The first conductive bodies 24a extend in a column direction of the arrangement in parallel to each other. One first conductive body 24a is assigned to each column of the elements 23. One first conductive body 24a is provided in common with respect to the piezoelectric films 26 of the elements 23 aligned in the column direction of the arrangement. Both ends of the first conductive body 24a are connected to a pair of extraction wirings 27, respectively. The extraction wirings 27 extend in a row direction of the arrangement in parallel to each other. Therefore, all the first conductive bodies 24a have the same length. In this manner, the lower electrode 24 is provided in common with respect to the elements 23 of the entire matrix.

The upper electrode 25 has a plurality of second conductive bodies 25a. The second conductive bodies 25a extend in a row direction of the arrangement in parallel to each other. One second conductive body 25a is assigned to each row of the elements 23. One second conductive body 25a is provided in common with respect to the piezoelectric films 26 of the elements 23 aligned in the row direction of the arrangement. Power distribution to the elements 23 is switched for each row. Line scanning or sector scanning is achieved corresponding to such switching of power distribution. Since the elements 23 in one row output ultrasonic waves at the same time, the number of the elements 23 in one row, that is, the number of columns of the arrangement can be determined based on the output level of ultrasonic waves. For example, the number of columns may be set to be around 10-15. In the drawing, five columns are illustrated for simplicity. The number of row s of the arrangement can be determined based on the extent of an area to be scanned. For example, the number of row s may be set to be 128 or 256. In the drawing, eight rows are illustrated for simplicity. Also, regarding the arrangement, a zigzag pattern may be used. In the zigzag pattern, a group of the elements 23 in an even row may be displaced with respect to a group of the elements 23 in an odd row by one-half of the column pitch. The number of the elements in one of an odd row and an even row may be smaller than the number of the elements in the other of an odd row and an even row by one. Furthermore, the role of the lower electrode 24 and the role of the upper electrode 25 may be switched. Specifically, the upper electrode may be connected in common to the elements 23 of the entire matrix, and the lower electrode may be connected in common to the elements 23 in each row of the arrangement.

The outer edge of the substrate 21 has a first side 21a and a second side 21b that are opposed and partitioned by a pair of straight lines 29 parallel to each other. In the peripheral region 31 that extends between the outline of the element array 22 and the outer edge of the substrate 21, a first terminal array 32a of one line is arranged between the first side 21a and the outline of the element array 22, and a second terminal array 32b of one line is arranged between the second side 21b and the outline of the element array 22. One line of the first terminal array 32a can be formed parallel to the first side 21a. One line of the second terminal array 32b can be formed parallel to the second side 21b. The first terminal array 32a is constructed of a pair of lower electrode terminals 33 and a plurality of upper electrode terminals 34. Similarly, the second terminal array 32b is constructed of a pair of lower electrode terminals 35 and a plurality of upper electrode terminals 36. The lower electrode terminals 33 and 35 are connected to both ends of each of the extraction wiring 27, respectively. It is sufficient for the extraction wirings 27 and the lower electrode terminals 33 and 35 to be formed plane-symmetrically with respect to a vertical plane that bisects the element array 22. The upper electrode terminals 34 and 36 are connected to both ends of each of the second conductive bodies 25a, respectively. It is sufficient for the second conductive bodies 25a, the upper electrode terminals 34 and 36 to be formed plane-symmetrically with respect to the vertical plane that bisects the element array 22. Here, the outline of the substrate 21 is formed in a rectangle. The outline of the substrate 21 may also be square or trapezoidal.

A first flexible printed substrate 37 is coupled with the substrate 21. The first flexible printed substrate 37 covers the first terminal array 32a. Conductive lines, that is, first signal lines 38 are formed at one end of the first flexible printed substrate 37 corresponding to the lower electrode terminals 33 and the upper electrode terminals 34, respectively. The first signal lines 38 are respectively opposed to the lower electrode terminals 33 and the upper electrode terminals 34, and respectively bonded thereto. Similarly, a second flexible printed substrate 41 covers the substrate 21. The second flexible printed substrate 41 covers the second terminal array 32b. Conductive lines, that is, second signal lines 42 are formed at a first end 41a of the second flexible printed substrate 41 corresponding to the lower electrode terminals 35 and the upper electrode terminals 36, respectively. The second signal lines 42 are respectively opposed to the lower electrode terminals 35 and the upper electrode terminals 36, and respectively bonded thereto.

Figure 4:
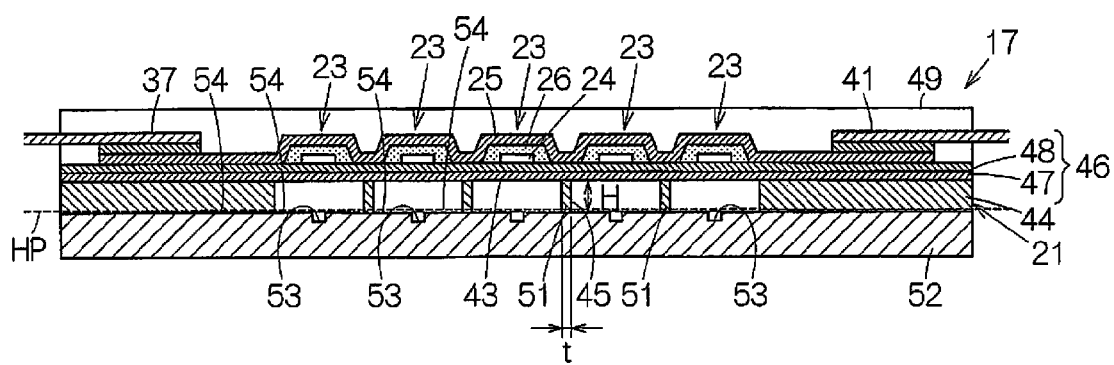
FIG. 4 is a sectional view along line 4-4 of FIG. 3.

As shown in FIG. 4, each of the elements 23 has a vibrating film 43. When constructing the vibrating film 43, an opening 45 is formed in each of the elements 23 on a substrate base 44 of the substrate 21. The openings 45 are arranged in an array pattern with respect to the substrate base 44. A flexible film 46 is formed on the entire surface (first surface) of the substrate base 44. The flexible film 46 is constructed of a silicon oxide ($SiO_2$) layer 47 layered on the surface of the substrate base 44, and a zirconium oxide ($ZrO_2$) layer 48 layered on a surface of the silicon oxide layer 47. The flexible film 46 contacts the openings 45. In this manner, a part of the flexible film 46 serves as the vibrating film 43 corresponding to the outline of the opening 45. The film thickness of the silicon oxide layer 47 can be determined based on the resonance frequency.

The lower electrode 24, the piezoelectric film 26, and the upper electrode 25 are layered on a surface of the vibrating film 43 in this order. For the lower electrode 24, a layered film of titanium (Ti), iridium (Ir), platinum (Pt), and titanium (Ti) can be used, for example. The piezoelectric film 26 may be formed of piezoelectric zirconate titanate (PZT), for example. The upper electrode 25 may be formed of iridium (Ir), for example. Another conductive material may be used for the lower electrode 24 and the upper electrode 25, and another piezoelectric material may be used for the piezoelectric film 26. Here, the piezoelectric film 26 completely covers the lower electrode 24 under the upper electrode 25. The function of the piezoelectric film 26 prevents short circuits between the upper electrode 25 and the lower electrode 24.

A protective film 49 is layered on the surface of the substrate 21. The protective film 49 covers, for example, the entire surface of the substrate 21. As a result, the protective film 49 covers the element array 22, the first terminal array 32a, the second terminal array 32b, a first end 37a of the first flexible printed substrate 37, and the first end 41a of the second flexible printed substrate 41. For example, a silicone resin film may be used for the protective film 49. The protective film 49 protects the configuration of the element array 22, the bonding of the first terminal array 32a and the first flexible printed substrate 37, and the bonding of the second terminal array 32b and the second flexible printed substrate 41.

Partition walls 51 are laid out between the adjacent openings 45. The openings 45 are partitioned by the partition walls 51. The wall thickness "t" of the partition wall 51 corresponds to the interval between the hollow spaces of the openings 45. The partition wall 51 defines two wall surfaces in planes extending in parallel to each other. The wall thickness "t" of the partition wall 51 corresponds to the interval between the wall surfaces. Specifically, the wall thickness "t" can be defined by the length of a vertical line that is orthogonal to the wall surfaces and sandwiched between the wall surfaces. The wall height "H" of the partition wall 51 corresponds to the depth of the opening 45. The depth of the opening 45 corresponds to the thickness of the substrate base 44. Therefore, the wall height "H" of the partition wall 51 can be defined as the length of the wall surface defined in the thickness direction of the substrate base 44. Since the substrate base 44 has a uniform thickness, the partition wall 51 can have a uniform wall height "H" over the entire length. When the wall thickness "t" of the partition wall 51 is decreased, the arrangement density of the vibrating film 43 can be increased. This can contribute to downsizing of the element chip 17. When the wall height "H" of the partition wall 51 is larger than the wall thickness "t", the bending rigidity of the element chip 17 can be increased. Consequently, the interval between the openings 45 is set to be smaller than the depth of the opening 45.

A reinforcing plate (reinforcing member) 52 is fixed to a reverse surface (second surface) of the substrate base 44 on the opposite side of the surface of the substrate base 44. The reverse surface of the substrate base 44 is overlaid on a surface of the reinforcing plate 52. The reinforcing plate 52 covers the openings 45 with the reverse surface of the element chip 17. The reinforcing plate 52 may have a rigid base material. For example, the reinforcing plate 52 may be formed of a silicon substrate. The plate thickness of the substrate base 44 is set to be around 100 μm, and the plate thickness of the reinforcing plate 52 is set to be around 100-150 μm. Here, the partition walls 51 are bonded to the reinforcing plate 52. The reinforcing plate 52 is bonded to each of the partition walls 51 in at least one bonding region. An adhesive can be used for bonding. In addition to superimposing of the substrate base 44 and the reinforcing member 52, "overlaid" also includes lamination of a reinforcing material on the reverse surface of the substrate base 44, and connection of the substrate base 44 and the reinforcing plate 52 arranged opposite each other.

A plurality of linear grooves (groove parts) 53 are formed on the surface of the reinforcing plate 52. The grooves 53 divide the surface of the reinforcing plate 52 into a plurality of planes 54. The plurality of planes 54 expand within one hypothetical plane HP. The reverse surface of the substrate base 44 expands within that hypothetical plane HP. The partition wall 51 is bonded to the plane 54. The grooves 53 sink from the hypothetical plane HP. The cross section shape of the groove 53 can be a quadrangle, a triangle, a semicircle or another shape.

Figure 5:
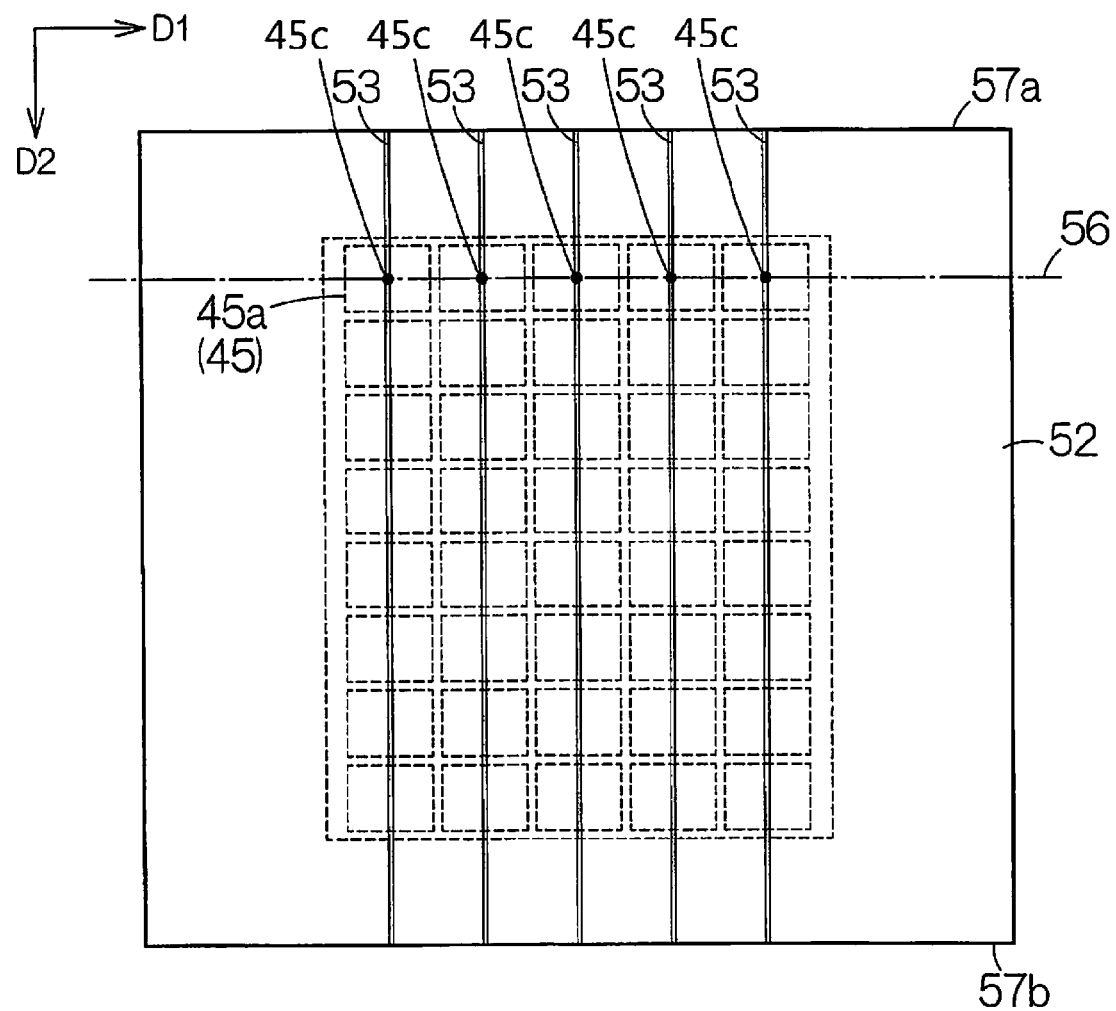
FIG. 5 is a plan view of a reinforcing plate showing grooves.

As shown in FIG. 5, the openings 45 form a line in a first direction D1. The centroids 45c of the outline shapes of the openings 45 are arranged at an equal pitch on a straight line 56 in the first direction D1. Since the openings 45 are formed by copying a single outline shape, the openings 45 of the same shape are arranged repeatedly at a uniform pitch. For example, an outline 45a of the opening 45 is defined as a quadrangle. Specifically, it is formed in a rectangle. The long side of the rectangle is made to coincide with the first direction D1. Since the opening 45 has a rectangular outline 45a in this way, the partition wall 51 can have a uniform wall thickness "t" over the entire length. In such an instance, the bonding region of the partition walls 51 may be a region that includes a center position of the long side. In particular, the bonding region of the partition walls 51 may be a region that includes the entire length of the long side. The partition walls 51 may be surface-bonded to the reinforcing plate 52 with respect to the entire surface between the openings 45 over the entire length of the long side. Also, the bonding region of the partition walls 51 may be located in at least one position of each side of the quadrangle. The bonding region of the partition walls 51 may continuously surround the quadrangle. The partition walls 51 may be surface-bonded to the reinforcing plate 52 with respect to the entire surface between the openings 45 over the entire periphery of the quadrangle.

The grooves 53 are aligned in the first direction D1 mutually parallel at a fixed interval. The grooves 53 extend in a second direction D2 that intersects with the first direction D1. Both ends of the grooves 53 open at the end surfaces 57a and 57b of the reinforcing plate 52. In a plan view seen from the direction orthogonal to the surface of the substrate 21, specifically, the thickness direction of the substrate 21, one groove 53 cuts across one line (here it is one column) of outlines 45a of the openings 45 in sequence. Each of the openings 45 has at least one groove 53 connected. Here, the second direction D2 is orthogonal to the first direction D1. Therefore, the grooves 53 cut across the outlines 45a of the openings 45 in the short side direction of the rectangle.

Figure 6:
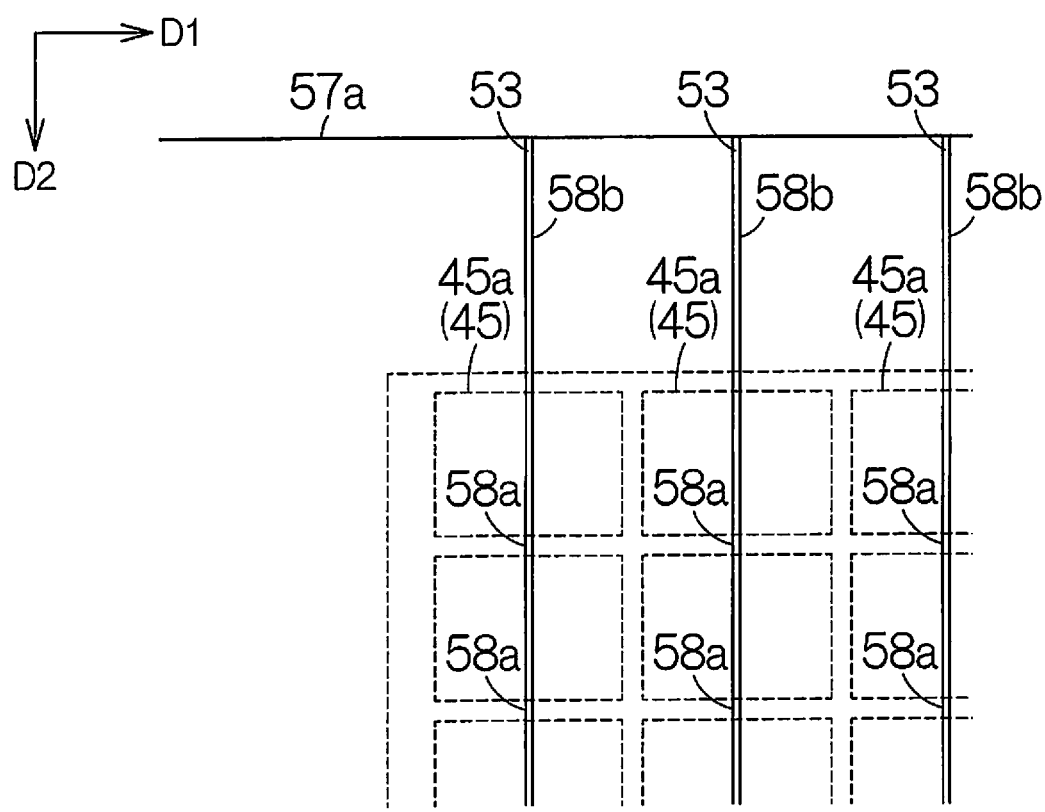
FIG. 6 is an enlarged partial plan view of FIG. 5.

As shown in FIG. 6, between the planes 54, the grooves 53 form ventilation passages 58a and 58b between the substrate base 44 and the reinforcing plate 52. In this way, the space within the groove 53 is made to communicate with the internal space of the opening 45. The ventilation passages 58a and 58b ensure mutual communication between the internal spaces of the openings 45 and the external space of the substrate 21. In a plan view seen from the thickness direction of the substrate 21, one groove 53 cuts across one line (here it is one column) of the outlines 45a of the openings 45 in sequence, so the openings 45 are connected successively by the ventilation passage 58a. Both ends of the groove 53 are open at the end surfaces 57a and 57b of the reinforcing plate 52. In this way, the ventilation passage 58b opens from the opening 45 of the line end to outside the outer edge of the substrate 21.

(3) Circuit Configuration of Ultrasonic Diagnostic Device

Figure 7:
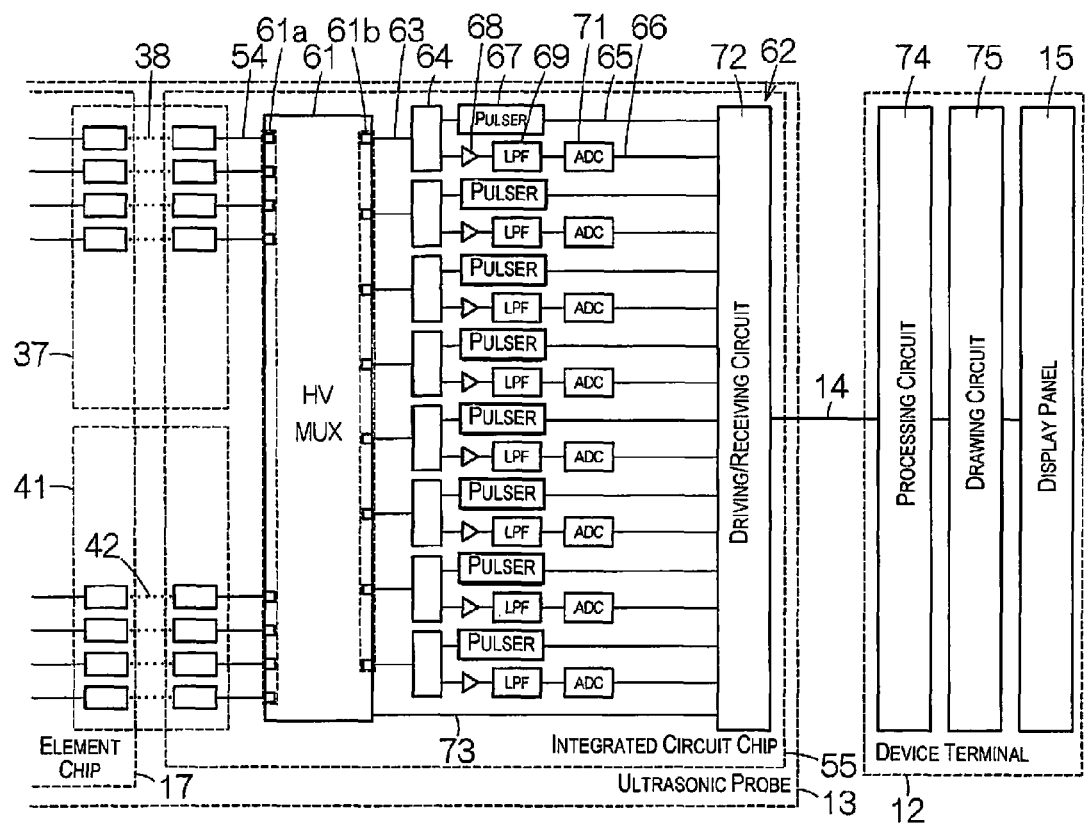
FIG. 7 is a block diagram schematically showing a circuit configuration of the ultrasonic diagnostic device.

As shown in FIG. 7, an integrated circuit has a multiplexer 61, and a transmitting and receiving circuit 62. The multiplexer 61 has a group of ports 61a on the element chip 17 side, and a group of ports 61b on the transmitting and receiving circuit 62 side. The first signal lines 38 and the second signal lines 42 are connected to the group of ports 61a via first wirings 54. In this manner, the group of ports 61a are connected to the element array 22. A prescribed number of signal lines 63 within the integrated circuit chip 55 are connected to the group of ports 61b on the transmitting and receiving circuit 62 side. The prescribed number corresponds to the number of rows of the elements 23 output simultaneously when scanning. The multiplexer 61 controls interconnection between the ports on the cable 14 side and the ports on the element chip 17 side.

The transmitting and receiving circuit 62 has a prescribed number of changing switches 64. The changing switches 64 are connected to the corresponding signal lines 63, respectively. The transmitting and receiving circuit 62 has a transmission channel 65 and a reception channel 66 for each of the changing switches 64. The transmission channel 65 and the reception channel 66 are connected to the changing switch 64 in parallel. The changing switch 64 selectively connects the transmission channel 65 and the reception channel 66 to the multiplexer 61. A pulser 67 is incorporated in the transmission channel 65. The pulser 67 outputs a pulse signal at a frequency corresponding to the resonance frequency of the vibrating film 43. An amplifier 68, a low-pass filter (LPF) 69, and an analog-digital converter (ADC) 71 are incorporated in the reception channel 66. A detection signal of each of the elements 23 is amplified, and converted into a digital signal.

The transmitting and receiving circuit 62 has a driving/receiving circuit 72. The transmission channel 65 and the reception channel 66 are connected to the driving/receiving circuit 72. The driving/receiving circuit 72 controls the pulser 67 simultaneously depending on the state of scanning. The driving/receiving circuit 72 receives a digital signal of a detection signal depending on the state of scanning. The driving/receiving circuit 72 is connected to the multiplexer 61 through a control line 73. The multiplexer 61 conducts control of interconnection based on a control signal supplied from the driving/receiving circuit 72.

A processing circuit 74 is incorporated in the device terminal 12. The processing circuit 74 can be provided with a central processing unit (CPU) 74 and a memory, for example. The entire operation of the ultrasonic diagnostic device 11 is controlled in accordance with processing of the processing circuit 74. The processing circuit 74 controls the driving/receiving circuit 72 in accordance with instructions input by a user. The processing circuit 74 generates an image in accordance with a detection signal of the element 23. The image is specified by drawing data.

A drawing circuit 75 is incorporated in the device terminal 12. The drawing circuit 75 is connected to the processing circuit 74. The display panel 15 is connected to the drawing circuit 75. The drawing circuit 75 generates a driving signal in accordance with drawing data generated in the processing circuit 74. The driving signal is sent to the display panel 15. As a result, an image is displayed on the display panel 15.

(4) Operation of Ultrasonic Diagnostic Device

Next, the operation of the ultrasonic diagnostic device 11 will be explained briefly. The processing circuit 74 gives the driving/receiving circuit 72 instructions to transmit and receive ultrasonic waves. The driving/receiving circuit 72 supplies a control signal to the multiplexer 61, and supplies a driving signal to each of the pulsers 67. The pulser 67 outputs a pulse signal in response to the supply of the driving signal. The multiplexer 61 connects the port of the group of ports 61a to the port of the group of ports 61b in response to the instructions of the control signal. The pulse signal is supplied to the elements 23 for each row through the lower electrode terminals 33, 35 and the upper electrode terminals 34, 36 in response to the selection of the port. The vibrating film 43 vibrates in response to the supply of the pulse signal. As a result, desired ultrasonic waves are emitted toward a target (for example, the inside of a human body).

After ultrasonic waves are transmitted, the changing switch 64 is switched. The multiplexer 61 maintains the connection relation of the ports. The changing switch 64 establishes a connection between the reception channel 66 and the signal line 63 instead of a connection between the transmission channel 65 and the signal line 63. Reflected waves of ultrasonic waves vibrate the vibrating film 43. As a result, a detection signal is output from the element 23. The detection signal is converted into a digital signal, and sent into the driving/receiving circuit 72.

Transmission and reception of ultrasonic waves are repeated. For repeating transmission and reception of ultrasonic waves, the multiplexer 61 changes the connection relation of the ports. As a result, line scanning or sector scanning is achieved. When scanning is finished, the processing circuit 74 generates an image based on the digital signal of the detection signal. The generated image is displayed on the screen of the display panel 15.

In the element chip 17, the element 23 can be formed to be thin. The element 23 can be formed on the thin substrate 21. Even in a case where the reinforcing plate 52 is fixed to the substrate 21, the element chip 17 can be formed to be thin. At the same time, the reinforcing plate 52 reinforces the strength of the substrate 21. In particular, since the wall thickness "t" is smaller than the wall height "H" in the partition wall 51, sufficient rigidity of the partition wall 51 can be obtained in the thickness direction of the substrate 21 due to the section modulus. Force in the thickness direction of the substrate 21 can be transmitted through the partition wall 51 and supported by the reinforcing plate 52. In this manner, the element chip 17 has sufficient strength in the thickness direction of the substrate 21. Also, even when the plate thickness of the substrate 21 is set to be around 100 μm, for example, the reinforcing plate 52 can prevent the substrate 21 from being damaged. On the other hand, in a case where the element array is constructed of a bulk-type ultrasonic transducer element, the plate thickness of the substrate is set to be around several millimeters. Even when the reinforcing plate 52 is bonded, for example, the thickness of the element chip 17 can be reduced securely compared to the case where the element array is constructed of a bulk-type ultrasonic transducer element. In addition, since the acoustic impedance of the vibrating film 43 is close to that of a human body compared to a bulk-type ultrasonic transducer element, an acoustic impedance matching layer can be omitted in the element chip 17 unlike in the case of a bulk-type ultrasonic transducer element. Omission of the matching layer can further contribute to making the element chip 17 thinner.

The reinforcing plate 52 is bonded to each of the partition walls 51 in at least one bonding region. When the partition walls 51 are bonded to the reinforcing plate 52, the movement of the partition walls 51 is restricted by the reinforcing plate 52. Thus, vibration of the partition walls 51 can be prevented. As a result, crosstalk between the elements 23 can be prevented. Further, when the movement of the partition walls 51 is restricted, vibration of the partition walls 51 can be prevented from acting on ultrasonic vibration of the elements 23. Then, ultrasonic vibration in a clear vibration mode can be obtained in the elements 23. When vibration of the partition walls 51 is avoided, the amplitude of ultrasonic vibration can be prevented from being decreased. On the other hand, when the partition wall 51 moves, a distorted vibration mode having a lower frequency than the vertical vibration mode of the vibrating film 43 occurs. Furthermore, the kinetic energy of the vibrating film 43 decreases by the movement amount of the partition wall 51, and the amplitude of the vibration decreases.

At this time, though the spaces within the openings 45 are enclosed by the flexible film 46 (vibrating film 43) and the reinforcing plate 52, the grooves 53 ensure ventilation between the internal space of each opening 45 and the external space of the substrate 21. Therefore, the internal spaces of the openings 45 are not sealed tightly. As a result, the internal spaces of the openings 45 are connected to the atmospheric space. The internal space of the openings 45 can easily follow ambient pressure fluctuations. In this way, it is possible to reliably avoid damage to the elements 23. If by chance the internal space of the opening 45 is sealed airtight, there will be concern for damage to the ultrasonic transducer element due to pressure fluctuations. Here, the external space is the space separated from the internal space by the substrate 21, the flexible film 46, and the reinforcing plate 52, meaning that this is a significantly larger space than the internal space.

The bonding region of the partition walls 51 can be a region that includes a center position of the long side. Therefore, a part of the partition walls 51 in which the amplitude of vibration is large is bonded to the reinforcing plate 52. As a result, vibration of the partition walls 51 can be effectively prevented. Also, the bonding region of the partition walls 51 can be a region that includes the entire length of the long side. When the partition walls 51 are bonded to the reinforcing plate 52 over the entire length of the long side, vibration of the partition walls 51 can be securely prevented. Further, the partition walls 51 can be surface-bonded with respect to the entire surface between the openings 45 over the entire length of the long side. When the partition walls 51 are surface-bonded to the reinforcing plate 52 with respect to the entire surface between the openings 45 over the entire length of the long side, vibration of the partition walls 51 can be securely prevented.

It is sufficient that the bonding region of the partition walls 51 be located in at least one position of each side of the quadrangle. When the partition walls 51 are bonded to the reinforcing plate 52 in each side of the quadrangle, vibration of the partition walls 51 can be securely prevented. Also, the bonding region of the partition walls 51 can continuously surround the quadrangle. When the partition walls 51 are bonded to the reinforcing plate 52 with respect to the entire region of the quadrangle, vibration of the partition walls 51 can be securely prevented. Further, the partition walls 51 can be surface-bonded with respect to the entire surface between the openings 45 over the entire periphery of the quadrangle. When the partition walls 51 are surface-bonded to the reinforcing plate 52 with respect to the entire surface between the openings 45 over the entire periphery of the quadrangle, vibration of the partition walls 51 can be securely prevented.

Figure 8:
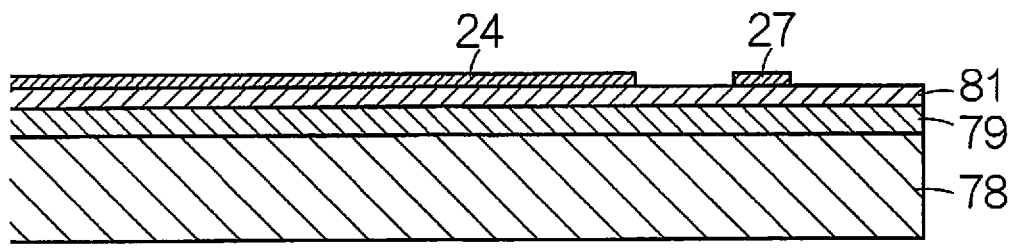
FIG. 8 is a partial enlarged vertical sectional view schematically showing a flexible film and a lower electrode formed on a silicon wafer.

(5) Method for Manufacturing Ultrasonic Transducer Element Chip of First Embodiment As shown in FIG. 8, the lower electrode 24, the extraction wiring 27, and the lower electrode terminals 33, 35 (not shown in the drawings subsequent to FIG. 8) are formed on a surface of a silicon wafer (substrate) 78 for each element chip 17. Prior to forming the lower electrode 24, the extraction wiring 27, and the lower electrode terminals 33, 35, a silicon oxide film 79 and a zirconium oxide film 81 are formed on the surface of the silicon wafer 78 successively. A conductive film is formed on a surface of the zirconium oxide film 81. The conductive film is constructed as a layered film of titanium, iridium, platinum, and titanium. The lower electrode 24, the extraction wiring 27, and the lower electrode terminals 33, 35 are formed from the conductive film by a photolithographic technique.

Figure 9:
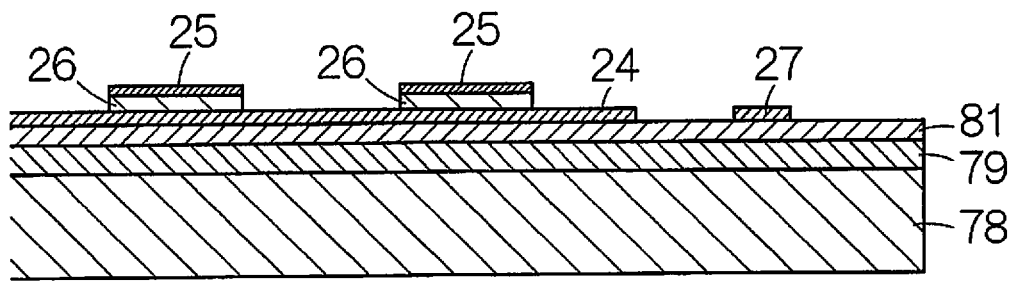
FIG. 9 is a partial enlarged vertical sectional view schematically showing a piezoelectric film and an upper electrode formed on the lower electrode.

As shown in FIG. 9, the piezoelectric film 26 and the upper electrode 25 are formed on a surface of the lower electrode 24 for each element 23. Prior to forming the piezoelectric film 26 and the upper electrode 25, a piezoelectric material film and a conductive film are formed on the surface of the silicon wafer 78. The piezoelectric material film is constructed of a PZT film. The conductive film is constructed of an iridium film. The piezoelectric film 26 and the upper electrode 25 are formed from the piezoelectric material film and the conductive film for each element 23 by a photolithographic technique.

Figure 10:
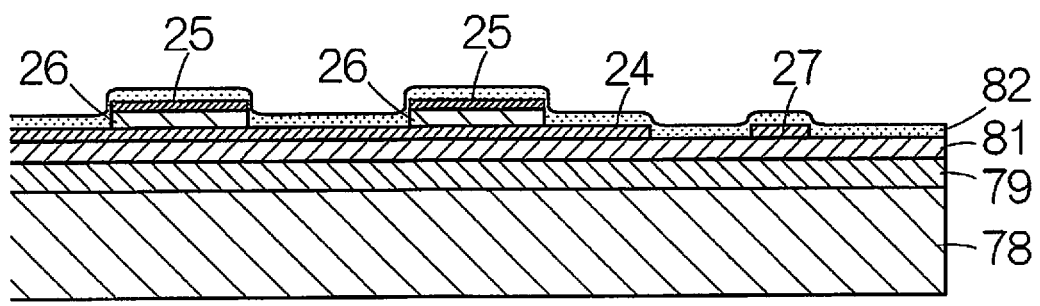
FIG. 10 is a partial enlarged vertical sectional view schematically showing a conductive film that covers the silicon wafer.

Next, as shown in FIG. 10, a conductive film 82 is formed on the surface of the silicon wafer 78. The conductive film 82 connects the upper electrodes 25 with respect to each other for each row in each element chip 17. Also, the upper electrode 25 and the upper electrode terminals 34, 36 are formed from the conductive film 82 by a photolithographic technique.

Figure 11:
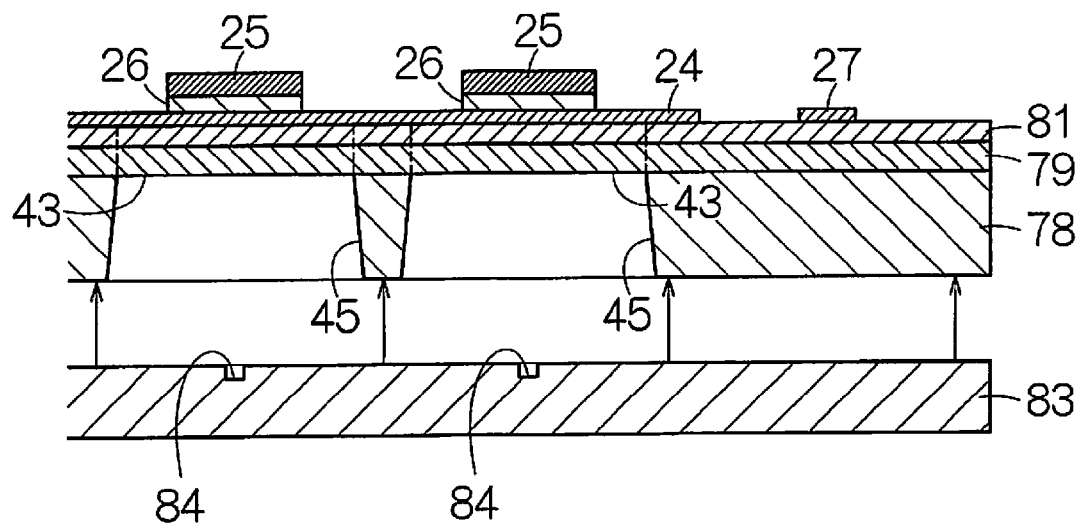
FIG. 11 is a partial enlarged vertical sectional view schematically showing an opening formed in the silicon wafer, and a reinforcing plate wafer.

Next, as shown in FIG. 11, the openings 45 of an array pattern are formed from the reverse surface of the silicon wafer 78. For forming the openings 45, an etching treatment is conducted. The silicon oxide film 79 serves as an etching stop layer. The vibrating film 43 is divided into the silicon oxide film 79 and the zirconium oxide film 81. After the openings 45 are formed, a surface of a reinforcing plate wafer 83 is superimposed on the reverse surface of the silicon wafer 78. For example, a rigid insulating substrate can be used for the wafer 83. A silicon wafer can be used for the insulating substrate. Before bonding, linear grooves 84 are formed on the surface of the reinforcing plate wafer 83. The grooves 84 extend in parallel to each other at equal intervals. At least one end of the groove 84 is open at the end surface of the wafer 83. An adhesive can be used for bonding, for example. After bonding, each of the element chips 17 is cut out of the silicon wafer 78. The grooves 84 provide the grooves 53.

When grooves 84 are formed in this way, even when the silicon wafer 78 and the wafer 83 are superimposed in air or in another gas atmosphere, superimposing can be achieved relatively easily. On the other hand, when the reverse surface of the silicon wafer 78 is superimposed on an even plane, the gas is pushed into each opening 45 interior by the plane of the reinforcing plate wafer. At atmospheric pressure, gas of greater volume than the volume of the space within the opening 45 tries to remain inside the openings 45. When extra gas does not escape from the interval between the silicon wafer 78 and the reinforcing plate wafer at the same time as sealing off of the openings 45, it is not possible to achieve binding together of the silicon wafer 78 and the reinforcing plate wafer.

(6) Ultrasonic Transducer Element Chip of Second Embodiment

Figure 12:
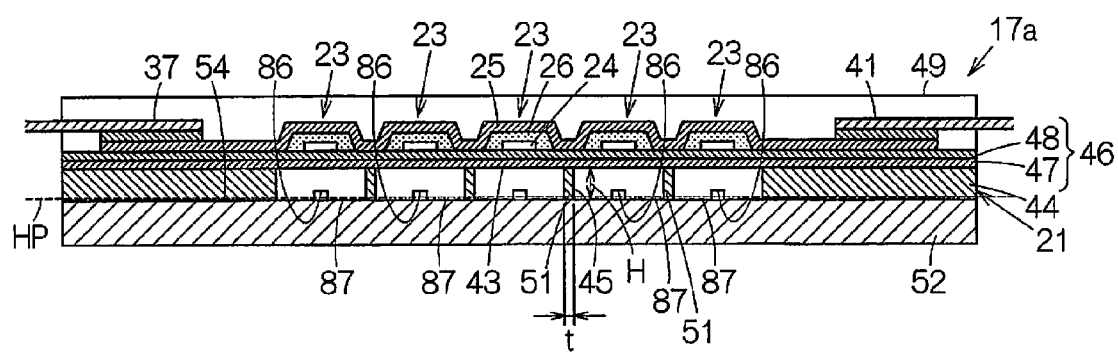
FIG. 12 is a vertical sectional view of an ultrasonic transducer element chip of the second embodiment corresponding to FIG. 4.
Figure 13:
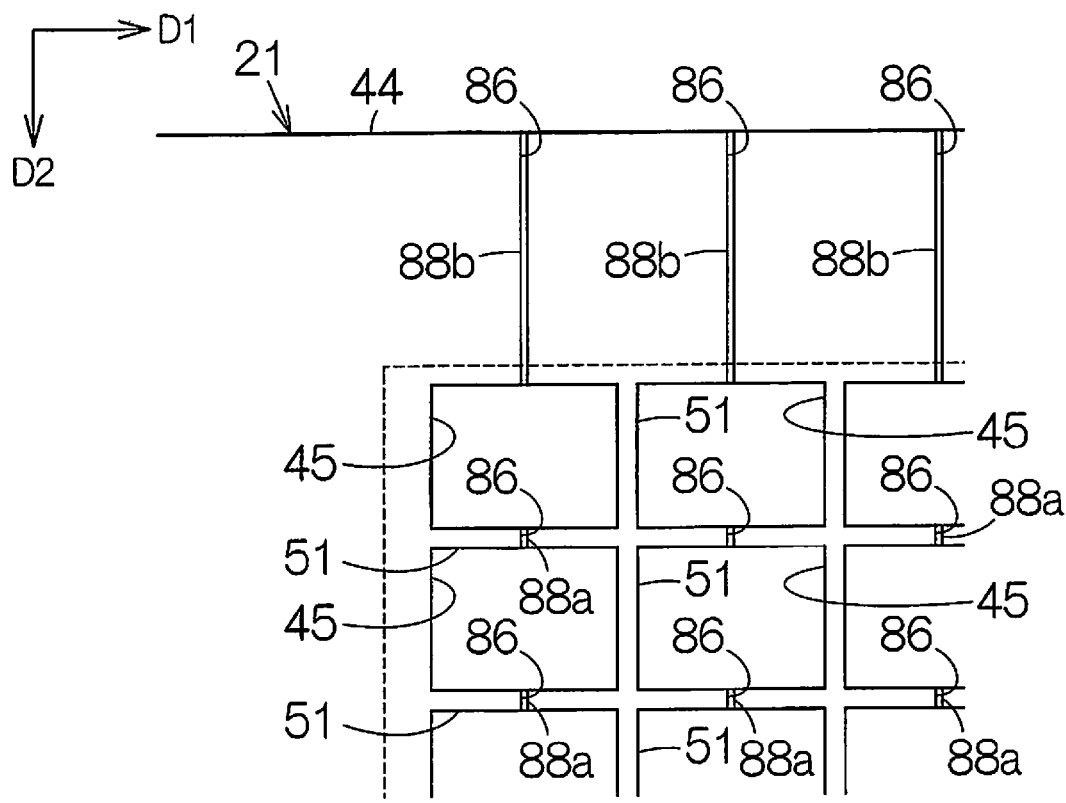
FIG. 13 is an enlarged partial plan view of an ultrasonic transducer element chip of the second embodiment corresponding to FIG. 6.

FIG. 12 schematically shows the ultrasonic transducer element chip 17a of the second embodiment. With this element chip 17a, a plurality of groove (groove parts) 86 are arranged on the reverse surface of the substrate 21. The grooves 86 divide the reverse surface of the substrate 21 at the bottom edge of the partition wall 51 into a plurality of planes 87. The plurality of planes 87 expand within one hypothetical plane HP. The surface of the reinforcing plate 52 expands within that hypothetical plane HP. The grooves 86 sink from the hypothetical plane HP. The cross section shape of the groove 86 can be a quadrangle, a triangle, a semi-circle or another shape. As shown in FIG. 13, the grooves 86 between the planes 87 form the ventilation passages 88a, 88b between the substrate base 44 and the reinforcing plate 52. In this way, the spaces within the grooves 86 are connected to the spaces within the openings 45. The ventilation passages 88a, 88b mutually connect inside and outside the spaces within the openings 45. In this way, ventilation is ensured between the space within the openings 45 and outside the openings 45. With one line (here it is one column) of openings 45, openings 45 are successively connected to each other by the ventilation passage 88a. The opening 45 of the line end and the outside of the outer edge of the substrate 21 are connected by the ventilation passage 88b. In this way, the opening 45 of the line end is open to the outside of the outer edge of the substrate 21. The remainder of the constitution can be constituted in the same manner as the element chip 17. In the drawing, equivalent constitutions and structures to those of the element chip 17 are given the same reference code numbers.

Figure 14:
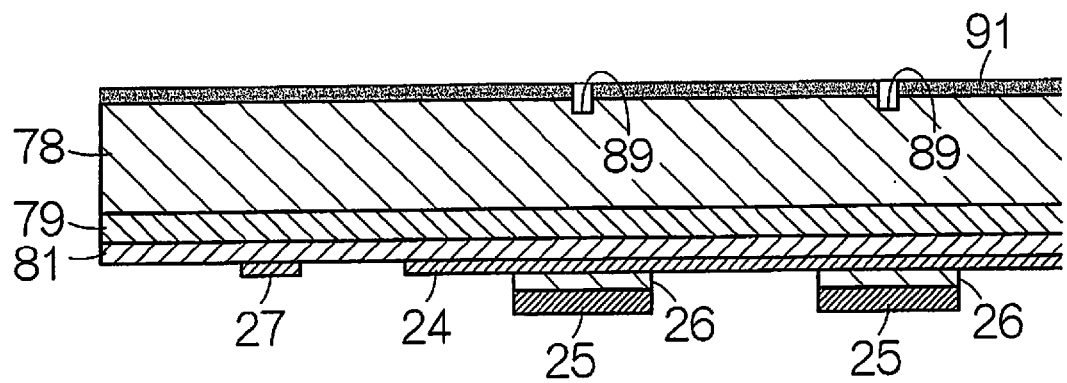
FIG. 14 is a partial enlarged vertical sectional view schematically showing a groove formed on the reverse surface of a silicon wafer.

As shown in FIG. 14, with the method of manufacturing the element chip 17a, before forming the openings 45, the grooves 89 are formed on the reverse surface of the silicon wafer 78. For forming the grooves 89, for example, a lithographic technique may be used. On the reverse surface of the silicon wafer 78, for example, a resist film 91 is formed. A pattern of the grooves 89 is formed on the resist film 91. In this way, when the grooves 89 are formed, the resist film 89 is removed. The same as in FIG. 10, an array of openings 45 is formed from the reverse surface of the silicon wafer 78. When each element chip 17a is cut out from the silicon wafer 78, the grooves 89 provide the grooves 86.

(7) Ultrasonic Transducer Element Chip of Third Embodiment

Figure 15:
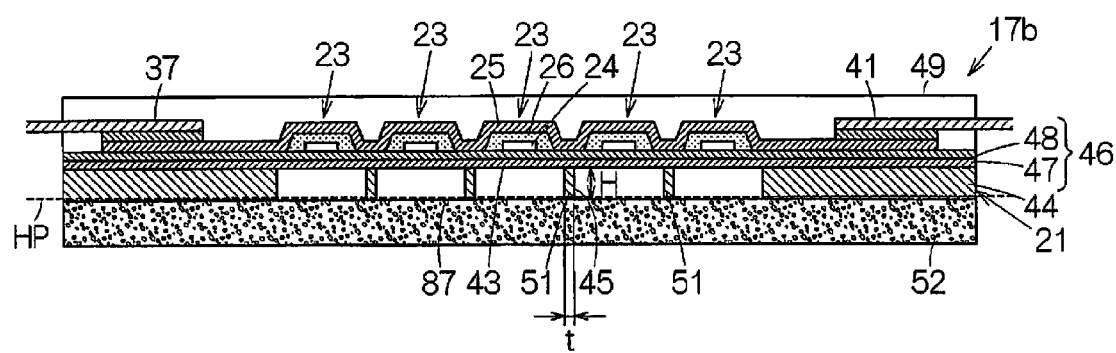
FIG. 15 is a vertical sectional view of an ultrasonic transducer element chip of the third embodiment corresponding to FIG. 4.

FIG. 15 schematically shows the ultrasonic transducer element chip 17b of the third embodiment. With this element chip 17b, at least a portion of one of the substrate 21 and the reinforcing plate 52 is constituted using a porous material. This kind of porous material is arranged at least between the openings 45 and between the opening 45 of the line end and the outer edge of the substrate 21. Here, the reinforcing plate 52 is formed from the porous material. The pores of the porous material are mutually and continuously lined so as to form the ventilation passages. The remainder of the constitution can be constituted in the same manner as the element chip 17. In the drawing, equivalent constitutions and structures to those of the element chip 17 are given the same reference code numbers.

While the present embodiment has been explained in detail as above, it will be apparent to those skilled in the art that various modifications can be made herein without substantially departing from the new matters and the effect of the present invention. Therefore, all such modifications are included in the scope of the invention. For example, the terms used in the specification or the drawings at least once together with a different term having a broader or similar meaning can be replaced with the different term in any portion of the specification or the drawings. Also, the configurations and operations of the ultrasonic diagnostic device 11, the ultrasonic probe 13, the probe head 13b, the element chips 17, 17a, and 17b, the element 23 and the like are not limited to the present embodiment, and various modifications are possible.

In the ultrasonic transducer element chip according to the embodiment, the ultrasonic transducer elements can be formed to be thin. The ultrasonic transducer elements can be formed in a thin substrate. Even in a case where the reinforcing member is fixed to a substrate, the ultrasonic transducer element chip can be formed to be thin. In addition, since the reinforcing member is fixed on the second surface of the substrate, it is possible for the strength of the substrate to be reinforced in the substrate thickness direction. At this time, the internal spaces of the openings are in communication with the external space of the substrate. Ventilation is ensured between the internal spaces of the openings and the external space of the substrate. Therefore, the internal spaces of the openings are not sealed tight. The internal spaces of the openings can easily follow ambient pressure fluctuations. In this way, it is possible to reliably avoid damage to the ultrasonic transducer element. If by chance the internal spaces of the openings are sealed airtight, there will be concern for damage to the ultrasonic transducer element due to pressure fluctuations.

The reinforcing member may be bonded to a partition wall section of the substrate between the openings in at least one bonding region. When the partition wall section is bonded to the reinforcing member, the movement of the partition wall section is restricted by the reinforcing member. Thus, vibration of the partition wall section can be prevented. As a result, crosstalk between the ultrasonic transducer elements can be prevented. Further, when the movement of the partition wall section is restricted, it is possible to avoid having the vibration of the partition wall section act on the ultrasonic vibration of the ultrasonic transducer elements. Then, ultrasonic vibration in a clear vibration mode can be obtained in the ultrasonic transducer elements. Consequently, when vibration of the partition wall section is avoided in this way, it is possible to inhibit a decrease in the amplitude of ultrasonic vibration.

The reinforcing member may include a first surface overlaid on the second surface of the substrate, and the ventilation passage includes a plurality of groove parts formed on the first surface of the reinforcing member. In this way, it is possible to ensure a ventilation passage relatively easily.

The ventilation passage may include a plurality of groove parts formed on the second surface of the substrate. In this way, it is possible to ensure a ventilation passage relatively easily.

At least a portion of one of the substrate and the reinforcing member may be made of a porous material, and the ventilation passage may include a plurality of pores of the porous material. In this way, it is possible to ensure a ventilation passage relatively easily.

The ultrasonic transducer element chip may be incorporated in a probe. The probe may be provided with the ultrasonic transducer element chip, and a case member supporting the ultrasonic transducer element chip.

The probe may be incorporated in an electronic instrument. The electronic instrument may be provided with a probe, and a processing circuit connected to the probe and configured to process output signals of the ultrasonic transducer elements.

Similarly, the probe may be incorporated in an ultrasonic diagnostic device. The ultrasonic diagnostic device may be provided with a probe, a processing circuit connected to the probe and configured to process output signals of the ultrasonic transducer elements to generate an image, and a display device configured to display the image.

The ultrasonic transducer element chip may be incorporated in a probe head. The probe head may be provided with an ultrasonic transducer element chip, and a case member supporting the ultrasonic transducer element chip, and configured to be coupled to a probe main body of a probe.

GENERAL INTERPRETATION OF TERMS

In understanding the scope of the present invention, the term "comprising" and its derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having" and their derivatives. Also, the terms "part," "section," "portion," "member" or "element" when used in the singular can have the dual meaning of a single part or a plurality of parts. Finally, terms of degree such as "substantially", "about" and "approximately" as used herein mean a reasonable amount of deviation of the modified term such that the end result is not significantly changed. For example, these terms can be construed as including a deviation of at least ±5% of the modified term if this deviation would not negate the meaning of the word it modifies.

While only selected embodiments have been chosen to illustrate the present invention, it will be apparent to those skilled in the art from this disclosure that various changes and modifications can be made herein without departing from the scope of the invention as defined in the appended claims. Furthermore, the foregoing descriptions of the embodiments according to the present invention are provided for illustration only, and not for the purpose of limiting the invention as defined by the appended claims and their equivalents.

What is claimed is:

1. An ultrasonic transducer element chip comprising:
a substrate defining an opening;
an ultrasonic transducer element disposed at a position corresponding to the opening in a thickness direction of the substrate; and
a reinforcing member connected to the substrate to cover the opening, the reinforcing member defining a ventilation passage from the opening to an outside of the substrate,
the substrate defining an additional opening with an additional ultrasonic transducer element being disposed at a position corresponding to the additional opening in the thickness direction of the substrate,
the reinforcing member being bonded to a partition wall section of the substrate between the opening and the additional opening, and
a wall thickness of the partition wall section being smaller than a wall height of the partition wall section.

2. The ultrasonic transducer element chip according to claim 1, wherein
the reinforcing member includes a first surface facing the substrate and defining a groove part that serves as the ventilation passage.

3. The ultrasonic transducer element chip according to claim 1, wherein
the reinforcing member defines the ventilation passage that is communicated with both the opening and the additional opening.

4. The ultrasonic transducer element chip according to claim 1, wherein
at least a portion of one of the substrate and the reinforcing member is made of a porous material, and
the ventilation passage includes a plurality of pores of the porous material.

5. The ultrasonic transducer element chip according to claim 1, wherein
the substrate is disposed between the ultrasonic transducer element and the reinforcing member in the thickness direction of the substrate.

6. A probe comprising:
the ultrasonic transducer element chip according to claim 1; and
a case member supporting the ultrasonic transducer element chip.

7. An electronic instrument comprising:
the probe according to claim 6; and
a processing circuit connected to the probe, and configured to process output signals of the ultrasonic transducer elements.

8. An ultrasonic diagnostic device comprising:
the probe according to claim 6;
a processing circuit connected to the probe, and configured to process output signals of the ultrasonic transducer elements to generate an image; and
a display device configured to display the image.

9. A probe head comprising:
the ultrasonic transducer element chip according to claim 1; and
a case member supporting the ultrasonic transducer element chip, and configured to be coupled to a probe main body of a probe.

10. The ultrasonic transducer element chip according to claim 1, wherein
each of the ultrasonic transducer element and the additional ultrasonic transducer element includes a first electrode, a piezoelectric film, and a second electrode, and
the piezoelectric film is positioned between the first electrode and the second electrode.

* * * * *